US00PP24182P2

(12) United States Plant Patent
Stemkens

(10) Patent No.: US PP24,182 P2
(45) Date of Patent: Jan. 21, 2014

(54) ***AUBRIETA* PLANT NAMED 'ABRZ0002'**

(50) Latin Name: *Aubrieta hybrida*
Varietal Denomination: ABRZ0002

(75) Inventor: Henricus Godefridus Wilhelmus Stemkens, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 88 days.

(21) Appl. No.: 13/507,192

(22) Filed: Jun. 12, 2012

(51) Int. Cl.
*A01H 5/00* (2006.01)

(52) U.S. Cl.
USPC ..... Plt./263.1

(58) Field of Classification Search
USPC ..... Plt./263.1
See application file for complete search history.

*Primary Examiner* — Susan McCormick Ewoldt
(74) *Attorney, Agent, or Firm* — Joshua L. Price

(57) ABSTRACT

A new *Aubrieta* plant named 'ABRZ0002' particularly distinguished by the light violet flowers, compact and mounded habit with good vigor, and is very winter hardy.

1 Drawing Sheet

Latin name of the genus and species of the plant claimed: *Aubrieta hybrida.*

Varietal denomination: 'ABRZ0002'.

BACKGROUND OF THE NEW PLANT

The present invention comprises a new *Aubrieta*, botanically known as *Aubrieta hybrida* and hereinafter referred to by the variety name 'ABRZ0002'.

'ABRZ0002' is a product of a planned breeding program. The new cultivar 'ABRZ0002' has light violet flowers, compact and mounded habit with good vigor, and is very winter hardy.

'ABRZ0002' originates from a hybridization in a controlled breeding program in a greenhouse in Enkhuizen, The Netherlands. The female parent was an unpatented, proprietary plant identified as 'G1424-52' with larger and darker flowers and less branching compared to 'ABRZ0002'.

The male parent of 'ABRZ0002' was an unpatented, proprietary plant identified as 'E0580-1' with darker flower color with an eye and larger leaves compared to 'ABRZ0002'. The resultant seed was sown in August 2007 in a greenhouse in Enkhuizen, The Netherlands.

'ABRZ0002' was selected as one flowering plant within the progeny of the stated cross in march 2008 in a greenhouse in Enkhuizen, The Netherlands.

The first act of asexual reproduction of 'ABRZ0002' was accomplished when vegetative cuttings were propagated from the initial selection in March 2008 in a greenhouse in Enkhuizen, The Netherlands.

BRIEF SUMMARY OF INVENTION

Horticultural examination of plants grown from cuttings of the plant initiated in March 2008 in Enkhuizen, The Netherlands, and continuing thereafter, has demonstrated that the combination of characteristics as herein disclosed for 'ABRZ0002' are firmly fixed and are retained through successive generations of asexual reproduction.

'ABRZ0002' has not been observed under all possible environmental conditions. The phenotype may vary significantly with variations in environment such as temperature, light intensity and day length.

A Plant Breeder's Right for this cultivar was applied for in Canada on Jun. 7, 2012, No. 12-7626. 'ABRZ0002' has not been made publicly available more than one year prior to the filing of this application.

The following traits have been repeatedly observed and are determined to be basic characteristics of the new variety. The combination of these characteristics distinguishes this *Aubrieta* as a new and distinct variety.

BRIEF DESCRIPTION OF THE PHOTOGRAPHS

The accompanying photographic drawings show typical flower and foliage characteristics of 'ABRZ0002' with colors being as true as possible with an illustration of this type.

Figure 1:
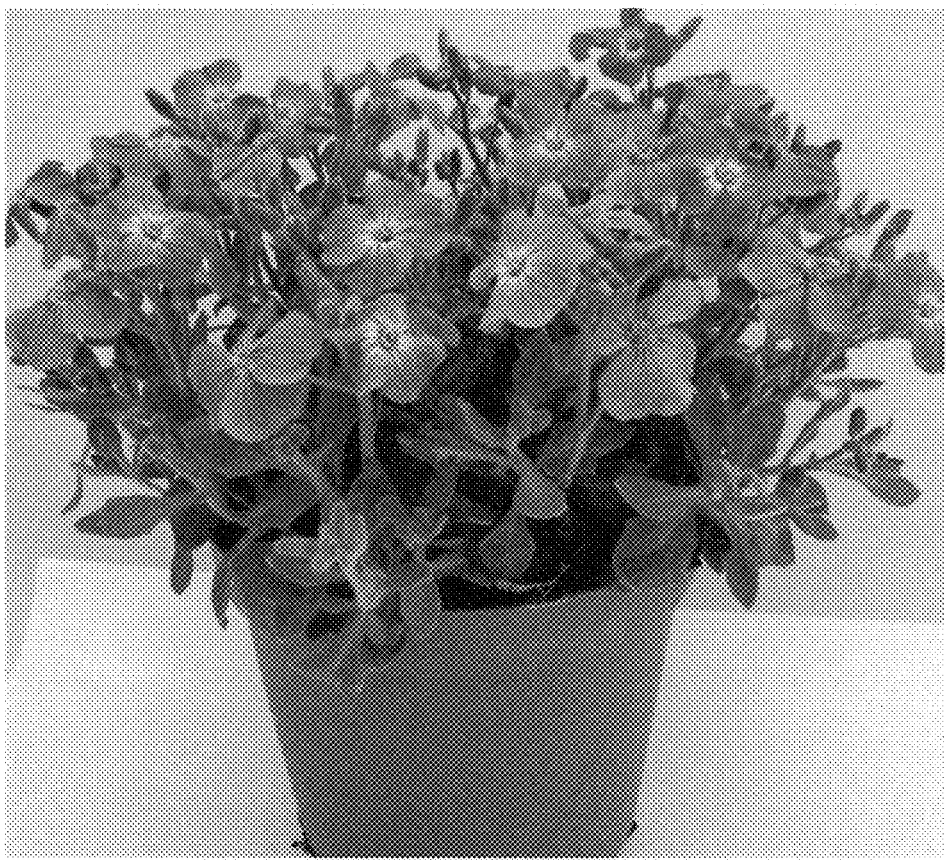
Figure 2:
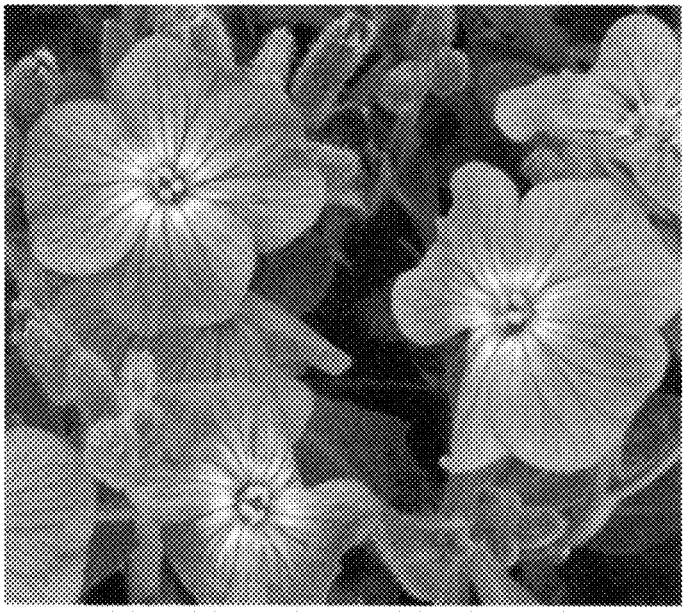

The photographic drawings show in FIG. 1 a flowering potted plant of the new variety and in FIG. 2 a close-up of the flowers.

DETAILED BOTANICAL DESCRIPTION

The plant descriptions and measurements were taken in Gilroy, Calif. under natural light in March 2012. These plants were approximately 22 week old and were growing in 1 gallon pots in shade-house trials.

The plants used for the photographs were about 26 weeks old growing in Enkhuizen, The Netherlands and the photographs were taken in March, 2012.

Color Chart used: Royal Horticultural Society Colour Chart (R.H.S.) 2001

TABLE 1

DIFFERENCES BETWEEN THE NEW VARIETY 'ABRZ0002' AND A SIMILAR VARIETY

| | 'ABRZ0002' | 'Audelbley' (U.S. Plant Pat. No. 18,468) |
|---|---|---|
| Flower color: | Light violet | More purple-violet with white eye |
| Foliage color: | Lighter green | Darker green |
| Foliage size: | Smaller | Larger |

Plant:

*Form, growth and habit.*—Compact, rounded, freely branching, freely flowering.

*Plant height.*—10.0 cm.

*Plant height (inflorescence included).*—17.0-20.0 cm.

*Plant width.*—30.0 cm.

Roots:

*Number of days to initiate roots.*—About 7 days at about 18 degrees C.

*Number of days to produce a rooted cutting.*—2.5 weeks at 18 degrees C.

*Type.*—Fine, fibrous, free branching.

*Color.*—RHS N155B but whiter.

Foliage:

*Arrangement.*—Alternate.

*Immature, leaf color, upper surface.*—Closest to and between RHS 143A and RHS 144A.

*Lower surface.*—Closest but lighter than RHS 143C.

*Mature, leaf color, upper surface.*—Closest to and deeper than RHS 143B.

*Lower surface.*—Closest to RHS 143C.

*Length.*—1.9-2.4 cm.

*Width.*—1.0-1.2 cm.

*Shape.*—Spathulate.

*Base shape.*—Attenuate.

*Apex shape.*—Mucronulate.

*Margin.*—Softly dentate.

*Texture, upper surface.*—Stellate hairs.

*Lower surface.*—Stellate hairs.

*Color of veins, upper surface.*—About the same as foliage color.

*Color of veins, lower surface.*—About the same as foliage color.

*Venation pattern.*—Pinnate.

*Petiole color.*—Closest to and between RHS 143A and RHS 144A.

*Length.*—1.0-1.1 cm.

*Diameter.*—0.3-0.4 cm.

*Texture.*—Stellate hairs and hirsute on both sides.

Stem:

*Color of stem.*—Closest to and between RHS 144B and RHS 145D.

*Length of stem.*—1.2-1.3 cm.

*Diameter.*—0.2 cm.

*Length of internodes.*—0.4-0.6 cm.

*Texture.*—Stellate hairs and hirsute.

*Color of peduncle.*—Closest to RHS 143B.

*Length of peduncle.*—5.0-14.0 cm.

*Peduncle diameter.*—0.2 cm.

*Texture.*—Stellate hairs and hirsute.

Inflorescence:

*Type.*—Single, cruciform, composed of 4 petals; flowers held above the plant.

*Quantity of inflorescences per plant.*—About 50 with as many buds.

*Lastingness of individual blooms on the plant.*—About 1 week.

*Fragrance.*—None.

Bud (just before opening/showing color):

*Color.*—RHS N88C to RHS N88D with RHS N88B veins.

*Length.*—1.4-1.5 cm.

*Width.*—0.3-0.4 cm.

*Shape.*—Oblong.

Corolla:

*Immature inflorescence.*—Diameter: 1.2-2.0 cm. Color of petals, upper surface: Lighter hue than RHS N88B with RHS N88B veining. Lower surface: RHS N88C to RHS N88D.

*Mature inflorescence.*—Flower diameter: 2.4-2.6 cm. Depth: 1.5 cm. Petal color, upper surface: Closest to and between RHS N88B and RHS N87B fading to About RHS N88C to RHS N87C with RHS 155C at the throat, with RHS 150C to RHS 150D basally and veining of about RHS N88A to RHS N88B. Lower surface: Closest to RHS N88C. Length of petal: 2.1-2.3 cm. Width of petal: 1.4-1.5 cm. Shape: Spathulate. Apex shape: Truncate, some even slightly retuse. Margin: Entire, and somewhat wavy. Petal texture, upper surface: Papillose. Lower surface: Papillose. Corolla tube color inside: RHS 150C to RHS 150D. Tube color outside: RHS 157C. Corolla texture, inside: Papillose. Outside: Papillose.

Calyx:

*Quantity.*—4.

*Color, upper surface.*—RHS 144B with a slightly darker apex.

*Lower surface.*—RHS 144B with a slightly darker apex.

*Length.*—1.0 cm.

*Width.*—0.15 cm.

*Shape.*—Oblong.

*Apex shape.*—Acute.

*Base.*—Fused.

*Margins.*—Entire.

*Texture, upper/inner surface.*—Smooth.

*Lower/outer surface.*—Long stellate hairs.

Reproductive organs:

*Gynoecium.*—

*Pistil quantity.*—1.

*Length.*—0.9 cm.

*Style color.*—RHS 144B.

*Style length.*—0.4-0.5 cm.

*Stigma color.*—RHS 144C.

*Stigma shape.*—Disc-shaped.

*Ovary color.*—RHS 144B and very pubescent so that it appears lighter.

*Ovary height.*—0.3 cm.

*Ovary width.*—0.075 cm.

*Androecium.*—

*Stamens, quantity.*—6.

*Color of filaments.*—RHS 155B.

*Length filaments.*—0.8-1.1 cm.

*Anther color.*—: RHS 11C.

*Anther length.*—0.1 cm.

*Anther shape.*—Ovate.

*Color of pollen.*—RHS 4B to RHS 4C.

*Pollen amount.*—Normal.

*Fertility/seed set.*—Has not been determined to date.

*Disease/pest resistance.*—Has not been determined to date.

What is claimed is:

1. A new and distinct variety of *Aubrieta* plant named 'ABRZ0002' substantially as illustrated and described herein.

* * * * *